(12) United States Patent
Garland

(10) Patent No.: US 7,425,129 B2
(45) Date of Patent: Sep. 16, 2008

(54) CENTRIC STOP MECHANISM FOR DENTAL MODEL

(76) Inventor: James K. Garland, 3258 E. Seven Springs Dr., Sandy, UT (US) 84092

( * ) Notice: Subject to any disclaimer, the term of this patent is extended or adjusted under 35 U.S.C. 154(b) by 44 days.

(21) Appl. No.: 11/396,058

(22) Filed: Mar. 31, 2006

(65) Prior Publication Data

US 2006/0228665 A1    Oct. 12, 2006

Related U.S. Application Data

(60) Provisional application No. 60/669,337, filed on Apr. 6, 2005.

(51) Int. Cl.
*A61C 11/00* (2006.01)

(52) U.S. Cl. ........................................................ 433/60

(58) Field of Classification Search .................... 433/60, 433/61, 66, 67, 54, 57
See application file for complete search history.

(56) References Cited

U.S. PATENT DOCUMENTS

| | | | | | |
|---|---|---|---|---|---|
| 5,360,337 | A | * | 11/1994 | Westdyk | 433/64 |
| 5,934,901 | A | * | 8/1999 | Huffman | 433/54 |
| 2004/0013998 | A1 | * | 1/2004 | Jung et al. | 433/57 |

* cited by examiner

*Primary Examiner*—Melba Bumgarner
(74) *Attorney, Agent, or Firm*—Terry M. Crellin

(57) ABSTRACT

A removable centric stop mechanism 10 for use in a system for making dental restorations. The stop mechanism 10 includes an elongate stop member 11 that can be firmly attached or connected to the dental model and can further be removed from the dental model when so desired. The elongate stop member 11 further incorporates a threaded elongate member 36 that can be threaded to and fro in a bore 34 in the elongate stop member 11 to thereby adjust the effective length of the elongate stop member 11.

12 Claims, 2 Drawing Sheets

CENTRIC STOP MECHANISM FOR DENTAL MODEL

This application claims the benefit of U.S. Provisional Application No. 60/669,337, filed Apr. 6, 2005.

BACKGROUND OF THE INVENTION

1. Field of the Invention

The invention relates to solid centric stop mechanisms or apparatus which are used in locating solid centric location with a dental model system which includes a flexible articulation means. The present invention provides improved centric stop means for dental model systems that are similar to those disclosed in U.S. Pat. No. 5,846,076 and PCT Pub. No. US 2003/0207230 A1. The present invention discloses additional, new centric stop apparatus that is to be used with the dental models and articulation means that are disclosed in U.S. Pat. No. 5,846,076 and PCT Pub. No. US 2003/0207230 A1, and the complete disclosures in those publications are included herein by reference.

2. State of the Art Prior to the Invention

The present invention provides an improved centric stop mechanism that is used in locating solid centric location when a dental model is being used that incorporates flexible articulation members. As disclosed in U.S. Pat. No. 5,846,076 and PCT application No. PCT/US01/05683, the dental model can consist of two base stones that are cast from dental casting material. One leg of an articulation member is either encapsulated within the casting material (as in U.S. Pat. No. 5,846,076) as each of the base stones are being cast, or a base stone is cast on a tray that has a leg of an articulation member either formed integrally with the tray or firmly attached and connected to the tray. In either case, the leg of the articulation member projects from respective base stone, with the leg of the articulation member having a free end that extends from the respective base stone. The free end of the leg of one articulation member extending from one base stone is adapted to be pivotally connected to the free end of the leg of a complimentary articulation member extending from a complimentary base stone to form a dental model, wherein the two base stones of the dental model are restrained by the articulation member so that the two base stones can be pivoted about the pivot axis of the pivotal connection connecting the complimentary legs of the articulation members to replicate biting action between the upper teeth and lower teeth of the dental model. This procedure is well known now in the art and is explained in detail in my U.S. Pat. No. 5,846,076.

Inasmuch as the legs of the articulation member are elongate and relatively thin, they have at least some flexibility. The flexibility is advantageous when the technician desires to move the parts of the dental model in a grinding type motion to check proper alignment of the dental model during such a grinding motion. This grinding type motion is produced by moving the complimentary base stones so as to flex the legs of the articulation member to allow the base stones to move back and forth in a lateral grinding motion relative to each other.

However, when the technician attempts to bring the base stones together to establish proper centric occlusal positioning, any flexing of the legs of the articulation member that allows undesirable up and down movement of the base stones relative to each other due to such flexing of the legs as opposed to the pivotal movement of the respective pair of pivotally connected legs is highly undesirable. In particular, when teeth are being restored at the posterior end of the dental model and no occluded opposing teeth are present to create a natural stop, it becomes necessary to artificially create a vertical stop in order to prevent the over closure of the opposing model. Thus, the technician is able to create accurate solid vertical relationship of the opposing dentition that is being restored with a crown or bridge.

In recognizing the need for a vertical stop, artisans in the past have used the following ways to achieve such a stop. In one method, a vertical rod or shore is glued to the model or articulation frame or model base, with the rod being cut at the required length to prevent over closure of the opposing models. In a second method, a mound of model stone is placed at the area needed to stop over closure against opposing models. In a third method, a cast in place post is immersed into the wet model stone of the second cast model positioned against the opposing model at the required height to set the vertical stop position. All these previous methods are cumbersome and require extra time spent by the technician. These methods also frequently require readjustment procedures and are difficult to adjust or fine tune the final vertical elevation of the cast models.

3. Objectives of the Invention

It is a broad object of the present invention to provide a solid centric stop mechanism that prevents the base stones of a dental model from being moved to an improper position that might otherwise be allowed by improper up and down type flexing of the legs of the associated articulation member.

A principal object of the present invention is to provide a solid centric stop mechanism that is either removably attached to the base stone of the dental model or removably attached to a leg of an articulation member that is in turn firmly attached to or encased in the base stone of the dental model.

An equally important object of the present invention is to provide a centric stop mechanism that is removably attached to the dental model, with the stop mechanism being further provided with means for adjusting or fine tuning the final vertical positioning of the upper and lower base stones of the dental model.

SUMMARY OF THE INVENTION

The present invention provides a removable centric stop mechanism that greatly simplifies procedures and saves valuable time of the technician. The centric stop mechanism of the invention comprises a vertical stop member that can be firmly attached or connected to the dental model and can further be removed from the dental model when it is not needed. In addition, the removable stop member of the present invention has means that allow for quickly and accurately adjusting and fine tuning the final vertical positioning of the base stones of the dental model.

In accordance with the present invention, a solid elongate centric stop member or locator is provided which can be removably affixed in some manner to the articulation member, the tray upon which the base stone is cast or to the base stone itself so that when affixed the stop member is firmly attached to the articulation member, the tray or the base stone, but when it is desired to remove the stop member it is readily removed with the ability to again be affixed to the articulation member, the tray or the base stone when so desired. When the stop member is affixed to the dental model, it provides means for locating solid centric location using the flexible articulation portion of the dental model.

The invention will be described in more particularity with reference to the accompanying drawings.

DESCRIPTION OF THE PREFERRED EMBODIMENTS

Figure 1:
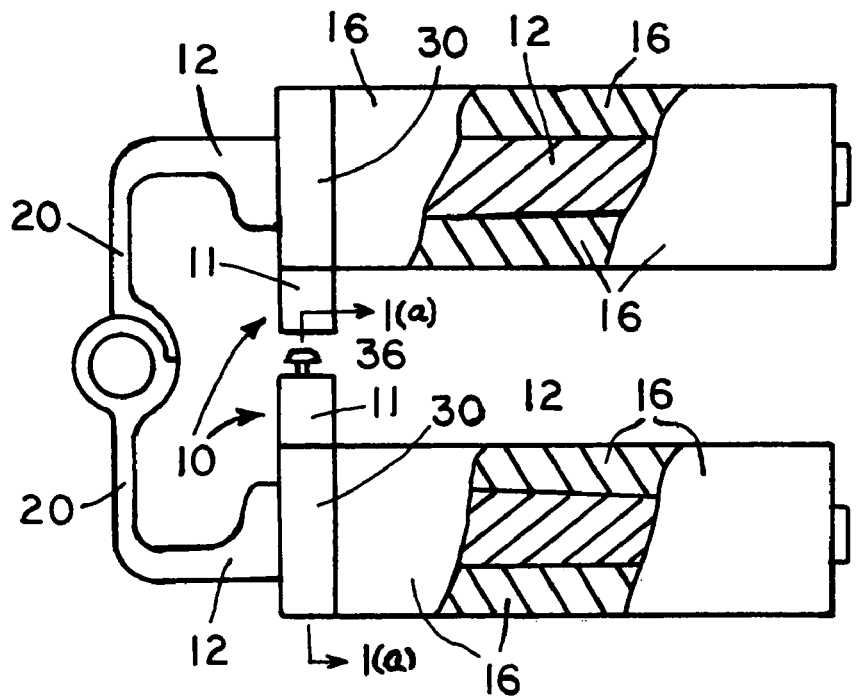
FIG. 1 is a side view of one embodiment of the stop member of the invention.

The removably attached elongate stop mechanism 10 of the present invention as shown in the drawings comprises an elongate stop element 11 that is removably attached to the base stone 16 or to a respective leg 12 of each of the articulation members of the articulation system by a mutually respective connector means that is in turn associated with either the base stone 16 or the leg 12 of the articulation member. The stop element 11 can be attached to and removed, repeatedly if so desired, from the base stone 16 or the leg 12 of the articulation member during the process of making a dental restoration or prosthesis.

Figure 2:
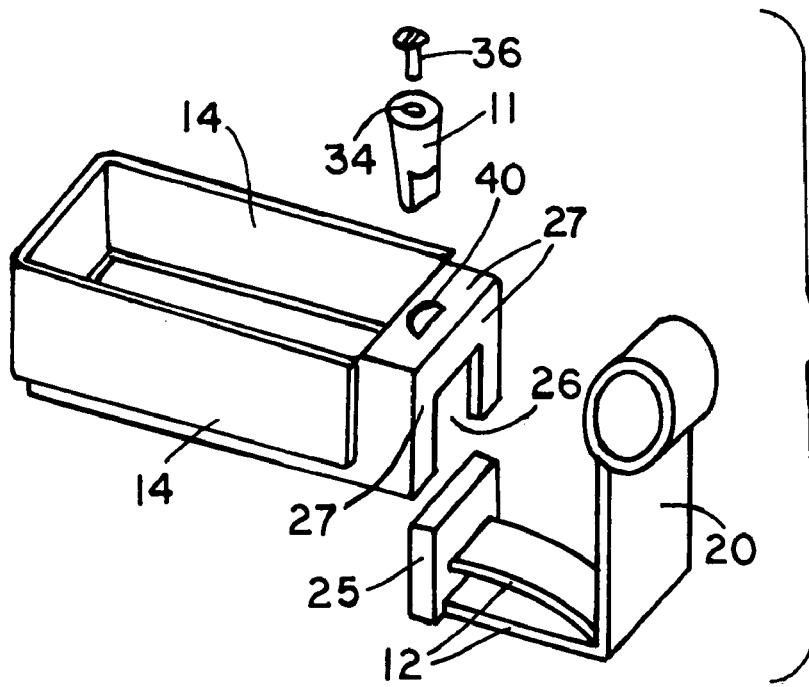
FIG. 2 is a pictorial view of a second embodiment of the invention.

The stop mechanism 10 of the present invention is used or incorporated into or with an articulation system such as or similar to the systems disclosed in my U.S. Pat. No. 5,846,076. Such articulation systems comprise mutually respective elongate legs 12, each of which has a first end which is firmly attached or connected to a base stone 16 of a dental model. The base stone 16 of the dental model can be cast directly around the first end of the leg 12 as shown in FIG. 1 or the first end of the leg 12 can be attached to or formed integrally with a tray 14. When a tray 14 is employed, the base stone is cast directly in the tray 14. The tray 14 can be molded integrally with the leg 12, or a mechanical connecting means can be used to securely attach the tray 14 to the first end of the leg 12 as shown in FIG. 2.

The second or other end of each leg 12 extends from the back end of the base stone 16 during the making of a dental model. The second end of each leg 12 has an arm 20 which is integrally formed therewith and extends substantially perpendicular to the longitudinal axis of leg 12 from the second end of the leg 12. A leg 12 and its attached arm 20 forms one member of the articulation system. The second member of the articulation system consists of a similar leg 12 and attached arm 20. The distal end of each arm 20 of one member of the articulation system has a connecting means that can be pivotally connected to a mutually respective connecting means on the distal end of the second member of the articulation system as illustrated in FIG. 1.

When using the system of the present invention, a mold corresponding to the lower teeth of a person is molded on the base stone 16 of the leg 12 of the first member of the articulation system, and a mold corresponding to the upper teeth of the person is molded on the base stone 16 of the leg 12 of the second member of the articulation system. The arm and leg members 20 and 12 of the first member of the articulation system are essentially similar to and substantially the same as the arm and leg members 20 and 12 of the second member of the articulation system, and the use of the two members of the articulation system in making a dental model is well known and described in my previously mentioned U.S. Pat. No. 5,846,076.

The elongate stop mechanism 10 of the present invention comprises a solid, elongate stop element 11 which is designed to be attached to and removed from the leg 12 of the articulation system. When the stop element 11 is attached to the leg 12 of the articulation system it is oriented so that the longitudinal axis of the stop element 11 extends away from the longitudinal axis of the leg 12 in the same general direction as does the arm 20, with the stop element 11 further being substantially perpendicular to a horizontal plane, generally called the occlusal plane.

Figure 1A:
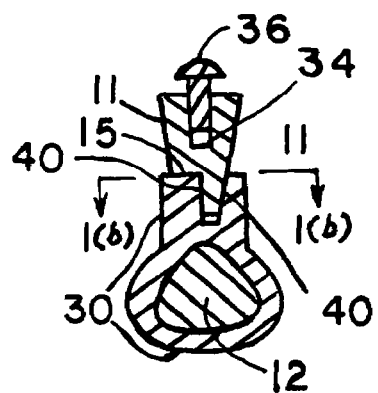
FIG. 1(a) is a cross section of the stop member of FIG. 1 taken along line 1(a)-1(a) of FIG. 1.
Figure 1B:
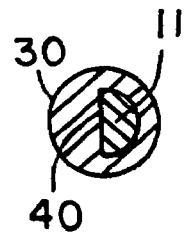
FIG. 1(b) is a cross section of the stop member of FIG. 1(a) taken along line 1(b)-1(b) of FIG. 1(a)

FIG. 1 is a side view of one embodiment of an articulation system in accordance with the present invention. FIGS. 1(a) and 1(b) are cross-sectional views taken along lines 1(a) of FIGS. 1 and 1(b), of FIG. 1(b), respectfully. As illustrated in FIGS. 1, 1(a) and 1(b) the stop mechanism 10 comprises a base member 30 that in itself is attached to the longitudinal, tapered leg 12 of the articulation member. The tapered leg 12 has a cross-sectional shape that is not round or circular, but instead angular, oval or other non-circular shape as is fully described in U.S. Pat. No. 5,846,076. The base member 30 of the stop mechanism 10 is attached to the tapered leg 12 by sliding longitudinally onto the tapered leg 12. As such, the base member 30 must have a central opening there through which has the same peripheral shape as the circumferential shape of the leg 12.

The opening in the base member 30 has a size that will allow it to slide onto the leg 12 and move into engagement with the tapered area of the leg 12 where the periphery of the leg 12 matches the periphery of the opening in the base member 30. The periphery of the base member 30 is sized so that the base member 30 will slide onto the leg 12 to a position that is near the end of the leg 12 to which the arm 20 extends. The base member 30 slides sufficiently along the leg 12 to be positioned so that the base stone 16 can be cast around and along the leg 12, with the base member 30 positioned adjacent to the back end of the base stone 16. It should, of course, be recognized that the base member 30 could be permanently affixed to the leg 12, as by gluing, or the base member 30 could actually be molded and formed as an integral, unitary part of the leg 12.

Means are provided on the base member 30 to accept the elongate stop element 11 so that the stop element 11 can be attached to and removed from the base member 30 repeatedly if so desired. The means for such attachment and detachment of the stop element 11 from the base member 30 as best shown in FIGS. 1(a) and 1(b) comprise a recessed receptacle 40 formed in the upper surface of the base member 30. The open receptacle 40 faces away from the longitudinal axis of the leg 12 of the articulation member, with the central axis of the receptacle 40 oriented substantially perpendicular to a horizontal plane, generally called the occlusal plane. The receptacle 40 has tapered sidewalls and the peripheral shape of the receptacle 40 is non-round or non-circular. Its peripheral shape can be oval or multi-sided or some similar non-circular shape, but as shown in FIG. 1(b), can in its simplest form, have the shape of a half circle. The purpose of the non-round or non-circular shape of the receptacle 40 will be further discussed hereinafter.

The elongate stop member 11 has a lower end portion that can be removably received into the receptacle 40. The lower end portion is itself elongate and tapers inwardly, i.e., gets smaller, in a direction downwardly toward its free end that is inserted into the receptacle 40. The peripheral shape of the lower portion of the stop member 11 is the same as the peripheral shape of the receptacle 40 and the sides of the lower portion of the stop member 11 taper at the same degree of slope as the taper in the sidewalls of the receptacle 40. As shown in FIG. 1(b), the lower portion of the elongate stop member 11 has a cross-sectional shape of a half circle, and as shown in FIG. 1(a), the lower portion of the elongate stop member 11 is tapered so as to fit snugly within the tapered receptacle 40. The purpose of the non-round shapes of the receptacle 40 and lower portion of the stop member 11 becomes evident. When inserted into the receptacle 40 the lower end portion of the stop member 11 can fit in only one orientation so that the stop member 11 is properly positioned and more importantly, the stop member 11 is held securely in its proper position so that it cannot rotate or turn on its longitudinal axis. The stop member 11 is in essence securely locked in its proper position and restrained from rotational movement when its lower end is fit snugly into the receptacle 40.

The upper end portion of the stop element 11 can be a simple extension of the lower end portion, but preferably has a shape that is sufficiently different and somewhat larger than the half circle shape of the lower end portion so that a flat abutment or seat 15 as shown in FIG. 1(a) is formed at the lower end of the upper end portion at the juncture of the lower end portion and upper end portion of the stop element 11. As further shown in FIG. 1(a), the upper end portion of the stop element 11 extends upwardly from the lower end portion. This upper end portion of the stop element 11 has a full circular cross-sectional shape, with the diameter of the circular shape at the junction between the lower end portion and the upper end portion being essentially the same as the diameter of the half circular shape of the lower end portion of the stop element 11.

As illustrated in FIG. 1(a), the sides of the upper end portion of the stop element 11 taper in the same fashion as do the sides of the lower end portion of the stop element 11. However, it should be recognized that the upper end portion of stop element 11 could have any cross-sectional shape and its side walls need not necessarily taper. The upper end portion must, of course, have a larger cross-sectional area than the cross-sectional area of the lower end portion of stop element 11 to provide the seat 15 as mentioned previously.

Figure 1C:
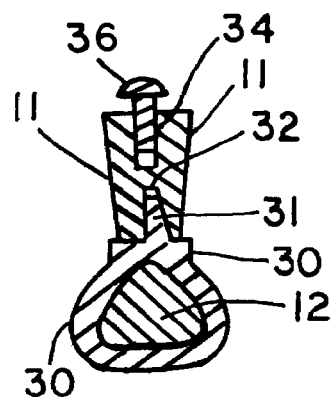
FIG. 1(c) is a cross section of a stop member similar to that of FIG. 1(a) taken along line 1(a)-1(a) of FIG. 1.

It should be recognized that the male-female relationship of the system for connecting the stop element 11 to the base member 30 as shown in FIG. 1(a) could be reversed as illustrated in FIG. 1(c). The base member 30 would incorporate a male projection element 31 that extends upwardly from the upwardly facing top of the base member 30. In that situation, the male projection 31 would be received in a female receptacle 32 that extends upwardly into the elongate stop element 11. The male and female elements 31 and 32 would have the same tapering features and relative sizes as discussed with the receptacle 40 and the lower end portion of the stop element 11 of FIGS. 1, 1(a) and 1(b).

The stop element 11 of the present invention has a bore 34 that extends inwardly from the top surface of the upper end portion of the stop element 11. A screw 36 is threaded into the bore 34. As shown in FIG. 1, when two articulation members are pivotally attached to each other with mutually respective molds of a patient's upper and lower teeth, the molds of the teeth can be moved toward and away from each other in a biting and chewing movement with the teeth being maintained in proper occlusal position when moved to the closed position by the stop element 11 as will now explained. The stop element 11 on the lower articulation member of FIG. 1 has the screw 36 threaded into the bore 34. The stop element 11 on the upper articulation member need not have such a screw threaded there into. The screw 36 on the lower articulation member can be adjusted in an out of the bore 34 so that the head of the screw 36 will engage the top of the mutually respective stop element 11 of the upper articulation member and form a stop in the movement of the upper teeth toward the lower teeth and maintain proper occlusal positioning of the teeth in that position. It should be recognized that the upper articulation member need not actually have a stop element 11. The screw 36 in the stop element 11 of the lower articulation member could be sufficiently long so that its extending end would engage the base stone 16 or even the leg 12 of the upper articulation member.

Another embodiment of the invention is shown in FIG. 2 where each member of the articulation system (only one such member being illustrated in FIG. 2) comprises an elongate lateral leg 12 similar to the leg 12 of FIG. 1, but a tray 14 extends from the leg 22. The base stone (not shown in FIG. 2) is cast in place in the tray 14. The tray 14 can be formed as an integral unit with the leg 22 or as shown in FIG. 2, the tray 14 can be formed so as to be integrally attached to the leg 22 by a connector having a slide element 25 that is received in a slot 26 in a relatively thick back side wall 27 of the tray 14. As in the articulation members of the articulation system of FIG. 1, the articulation member shown in FIG. 2 has an arm 20 that is integrally formed with the leg 22 and extends substantially perpendicular to the longitudinal axis of leg 22 from the free end of leg 22. The distal end of the arm 20 has connecting means that are adapted to pivotally engage the end of the arm 20 of a mutually corresponding articulation member to form a working articulation system.

In the embodiment of the invention as shown in FIG. 2, the back wall 27 functions as the base member of the stop member 10. A recessed receptacle 40 extends downwardly from the top surface of the back wall 27. The elongate stop element 11 is designed to slide into the open receptacle 40 so that the stop element 11 can be attached to and removed from the back wall 27 of the tray 14. The receptacle 40 and the stop element 11 and their inter-relationship and operation are in all respects similar to and the same as previously described with respect to the embodiment of the inventions shown in FIGS. 1, 1(a) and 1(b) and need no further description at this point.

It should be noted that the male-female relationship of the engagement between the back wall 27 and stop element 11 could be reversed in a manner as previously discussed with the embodiment of FIGS. 1, 1(a), 1(b) and 1(c). Accordingly, a male type connector could extend upwardly from the top of the back wall 27 of the tray 14, and a female type receptacle for receiving the male type connector could be recessed upwardly from the lower end of the stop element 11.

Figure 3:
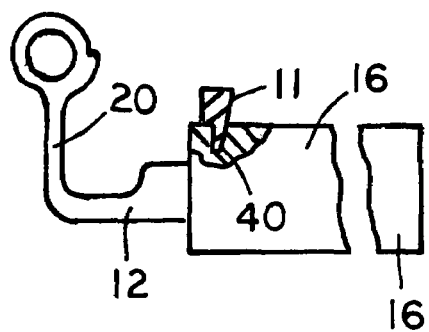
FIG. 3 is a side view of a third embodiment of the stop member of the invention.

In an alternative embodiment of the invention which is not presently considered to be as commercially valuable as the embodiments discussed heretofore, the receptacle 40 of the removable stop mechanism of the present invention could be formed directly in the base stone 16 of the dental model. As is shown diagrammatically and in cross-section in FIG. 3, the lower end portion of the stop element 11 can be pushed into the top surface of the green casting material of the base stone 16 as the base stone 16 is being cast. After the casting hardens, the stop element 11 can be removed from the base stone 16 so as to leave an open ended receptacle that the stop element 11 can be inserted into. This latter procedure is more time consuming than where the receptacle 40 is incorporated integrally into the elements that are used in making the articulation system, and in addition, the dental technician must exercise special care in properly positioning the stop element in the green casting material as the dental model is being cast.

The invention claimed is:

1. An articulation system used in making a dental restoration, wherein said articulation system includes (1) a lateral leg member that extends from a back end of a base stone that is firmly attached at a first end of said lateral leg member, (2) an arm member that extends from an opposite, second end of said lateral leg member in a direction away from an axis of said lateral leg member, and (3) a removably attached stop mechanism, wherein said stop mechanism comprises an elongate stop member having a first end portion and a second end portion that are joined together in axial alignment at a common juncture, wherein at said common juncture said second end portion has a larger cross-sectional area than a corresponding cross-sectional area of said first end portion so that a flat abutment surface is formed at said common juncture;

means for removably connecting said first end portion of said elongate stop member to said lateral leg member at a position adjacent to where said lateral leg member extends from said base stone so that said elongate stop member extends away from said lateral leg member in substantially the same general direction as said arm member extends away from said lateral leg member, wherein said means for removably connecting said first end portion of said elongate stop member to said lateral leg member comprises a recessed receptacle formed in a surface of said lateral leg member;

said recessed receptacle having an open top in an upper surface of said lateral leg member and sides extending from said open top into said lateral leg member;

said first end portion of said elongate stop member is received in said recessed receptacle with said flat abutment surface formed at said common juncture between said first end portion and said second end portion of said elongate stop member abutting said surface of said lateral leg member; and sidewalls of said first end portion of said elongate stop member having a peripheral size and shape so that said sidewalls are received within said recessed receptacle to make snug, secure engagement with said sides of said recessed receptacle and thereby hold said elongate stop member in a secure, firm position extending from said lateral leg member.

2. The articulation system in accordance with claim 1 wherein said recessed receptacle has a closed bottom, and when said first end portion of said elongate stop member is received within said recessed receptacle, a distal end surface of said first end portion of said elongate stop member is positioned close to said closed bottom of said recessed receptacle.

3. The articulation system in accordance with claim 1 wherein said recessed receptacle has a sidewall surface that slants inwardly toward a central axis of said recessed receptacle so that said recessed receptacle tapers inwardly in a direction extending away from said open top of said recessed receptacle; and said first end portion of said elongate stop member has a sidewall surface that slants outwardly from a central axis of said elongate stop member so that said first end portion of said elongate stop member tapers outwardly in a direction from a distal end surface of said first end portion of said elongate stop member to said common juncture with said second end portion of said elongate stop member, wherein said first end portion of said elongate stop member is received snugly within said recessed receptacle.

4. The articulation system of claim 1 wherein a distal end surface of said second end portion of said elongate stop member has a recessed bore extending inwardly therefrom in the direction of a central axis of said elongate stop member; and said elongate stop member further includes an elongate threaded member having a head end and a distal end, wherein said distal end of said threaded member can be screwed into said recessed bore in said second end portion of said elongate stop member to thereby adjust the effective length of said elongate stop member.

5. An articulation system used in making a dental restoration, wherein said articulation system includes (1) a lateral leg member (2) a base stone that is firmly attached at a first end of said lateral leg member so that said lateral leg member extends from a back end of said base stone, (3) an arm member extends from an opposite, second end of said lateral leg member in a direction away from an axis of said lateral leg member, and (4) a removably attached stop mechanism, wherein said stop mechanism comprises an elongate stop member having first and second ends; and means for removably connecting a first end of said elongate stop member to said base stone at a position adjacent to where said lateral leg member extends from said base stone so that said elongate stop member extends away from said base stone and lateral leg member in substantially the same general direction as said arm extends away from said lateral leg member.

6. The articulation system in accordance with claim 5 wherein said means for removably connecting said first end of said elongate stop member to said base stone comprises a recessed receptacle formed in a surface of said base stone; and said first end of said elongate stop member has a peripheral size and shape so that it can be received within said recessed receptacle, with a lower peripheral surface of said first end of said elongate stop member making a snug, secure engagement with said recessed receptacle to hold said elongate stop member in a secure, firm position extending from said base stone.

7. The articulation system in accordance with claim 6 wherein said recessed receptacle has a sidewall surface that slants inwardly toward a central axis of said recessed receptacle so that said recessed receptacle tapers inwardly in a direction from an open top of said recessed receptacle to a closed bottom of said recessed receptacle; and said first end of said elongate stop member has a sidewall surface that slants outwardly from a central axis of said elongate stop member so that said first end of said elongate stop member tapers outwardly in a direction from said first end of said elongate stop member to said second end of said elongate stop member, wherein said first end of said elongate stop member is received snugly within said recessed receptacle.

8. The articulation system in accordance with claim 5 wherein said means for removably connecting said first end of said elongate stop member to said base stone comprises a recessed receptacle formed in said first end of said elongate stop member and extending inwardly in the direction of a central axis of said elongate stop member; and a projection extending outwardly from the surface of said base stone, said projection having a peripheral size and shape so that said recessed receptacle of said elongate stop member can be received over said projection, with said recessed receptacle making a snug, secure engagement with said projection to hold said elongate stop member in a secure, firm position extending from said base stone.

9. The articulation system in accordance with claim 8 wherein said recessed receptacle has a sidewall surface that slants inwardly toward a central axis of said recessed receptacle so that said recessed receptacle tapers inwardly in a direction from an open bottom of said recessed receptacle to a closed top of said recessed receptacle; and said projection has a sidewall surface that slants inwardly toward a central axis of said projection so that said projection tapers inwardly in a direction extending away from said base stone, wherein said projection is received snugly within said recessed receptacle.

10. The articulation system of claim 5 wherein said second end of said elongate stop member has a recessed bore extending inwardly from said second end of said elongate stop member in the direction of a central axis of said elongate stop member; and said elongate stop member further includes an elongate threaded member having a head end and a distal end, wherein said distal end can be screwed into said bore in said second end of said elongate stop member to thereby adjust the effective length of said elongate stop member.

11. An articulation system used in making a dental restoration, wherein said articulation system includes (1) a lateral leg member that extends from a back end of a base stone that is firmly attached at a first end of said lateral leg member, (2) an arm member that extends from an opposite, second end of said lateral leg member in a direction away from an axis of said lateral leg member, and (3) a removably attached stop mechanism, wherein said stop mechanism comprises an elongate stop member having first and second ends;

means for removably connecting a first end of said elongate stop member to said lateral leg member at a position adjacent to where said lateral leg member extends from said base stone so that said elongate stop member extends away from said lateral leg member in substantially the same general direction as said arm member extends away from said lateral leg member, wherein said means for removably connecting said first end of said elongate stop member to said lateral leg member comprises a recessed receptacle in the form of a recessed well formed in said first end of said elongate stop member and extending inwardly in a direction of a central axis of said elongate stop member;

said recessed well having an open end in a distal surface of said first end of said elongate stop member, sides extending from said open end into said first end of said elongate stop member, and a closed recessed end; and a projection extending outwardly from a surface of said lateral leg member, said projection having a peripheral size and shape so that said recessed well of said elongate stop member can be received over said projection, with said recessed well making a snug, secure engagement with said projection to hold said elongate stop member in a secure, firm position extending from said lateral leg member.

12. The articulation system in accordance with claim 11 wherein said recessed well has side surfaces that slant inwardly toward a central axis of said recessed well so that said recessed well tapers inwardly in a direction from said open end of said recessed well to said closed end of said recessed well; and said projection has a sidewall surface that slants inwardly toward a central axis of said projection so that said projection tapers inwardly in a direction extending away from said lateral leg member, wherein said projection is received snugly within said recessed well.

\* \* \* \* \*